United States Patent [19]

Del Rossi

[11] Patent Number: 5,220,096
[45] Date of Patent: Jun. 15, 1993

[54] LIQUID ACID ALKYLATION CATALYST COMPOSITION AND ISOPARAFFIN:OLEFIN ALKYLATION PROCESS

[75] Inventor: Kenneth J. Del Rossi, Woodbury, N.J.

[73] Assignee: Mobil Oil Corporation, Fairfax, Va.

[21] Appl. No.: 719,276

[22] Filed: Jun. 21, 1991

[51] Int. Cl.$^5$ .............................................. C07C 2/62
[52] U.S. Cl. ................................... 585/724; 585/726; 585/730
[58] Field of Search ............... 585/722, 723, 724, 725, 585/726, 730

[56] References Cited

U.S. PATENT DOCUMENTS

| | | | |
|---|---|---|---|
| 2,406,954 | 9/1946 | Linn | 585/724 |
| 2,615,908 | 10/1952 | McCaulay et al. | 260/438 |
| 3,531,546 | 9/1970 | Hervert | 260/683.51 |
| 3,778,489 | 12/1973 | Parker et al. | 260/683.43 |
| 3,795,712 | 3/1974 | Torck et al. | 260/671 |
| 3,856,764 | 12/1974 | Throckmorton et al. | 260/82.1 |
| 3,865,896 | 2/1975 | McCoy et al. | 585/725 |
| 3,979,476 | 9/1976 | Kemp | 585/724 |
| 4,025,577 | 5/1977 | Siskin et al. | 260/683.51 |
| 4,065,381 | 12/1977 | Jay et al. | 585/724 |
| 4,094,924 | 6/1978 | Siskin et al. | 260/683.51 |
| 4,426,545 | 1/1984 | Kremer | 585/724 |
| 4,472,268 | 9/1984 | Olah | 585/725 |
| 4,636,488 | 1/1987 | Imai et al. | 502/172 |
| 4,646,488 | 3/1987 | Burns | 52/94 |
| 4,938,935 | 7/1990 | Audeh et al. | 423/240 |
| 4,938,936 | 7/1990 | Yan | 423/240 |
| 4,985,220 | 1/1991 | Audeh et al. | 423/240 |
| 5,073,674 | 12/1991 | Olah | 585/725 |

FOREIGN PATENT DOCUMENTS

| | | | |
|---|---|---|---|
| 0243923 | 3/1987 | Fed. Rep. of Germany | 585/725 |
| 0271322 | 8/1989 | Fed. Rep. of Germany | 585/725 |

OTHER PUBLICATIONS

"Alkylation of Isobutane with $C_4$ Olefins", 27 *Ind. Eng. Chem. Res., 381–397, (1988).*
"*Handbook of Petroleum Refining Processes*", 23–28 (R. A. Meyers, ed., 1986).

Primary Examiner—Asok Pal
Attorney, Agent, or Firm—Alexander J. McKillop; Dennis P. Santini; Robert B. Furr, Jr.

[57] ABSTRACT

The invention provides an isoparaffin:olefin alkylation catalyst composition comprising at least one acid selected from the group consisting of hydrofluoric acid and the halogen-substituted sulfonic acids, together with a carbonate additive having the formula ROC-(O)OR or

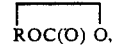

wherein R is selected from alkyl, alkyl halide, aromatic and halogenated aromatic groups having from about 1 to about 30 carbon atoms, and an isoparaffin:olefin alkylation process employing the same.

24 Claims, No Drawings

LIQUID ACID ALKYLATION CATALYST COMPOSITION AND ISOPARAFFIN:OLEFIN ALKYLATION PROCESS

CROSS REFERENCE TO RELATED APPLICATIONS

This application is related by disclosure of similar subject matter to the following U.S. patent applications:
Ser. No. 07/719,277, pending,
Ser. No. 07/720,124, pending,
Ser. No. 07/719,274, pending,
Ser. No. 07/719,278, pending,
Ser. No. 07/720,125, and
Ser. No. 07/719,879, pending,
all filed on even date herewith.

FIELD OF THE INVENTION

The present invention relates to the art of catalytic alkylation. The invention relates to a liquid alkylation catalyst and an isoparaffin:olefin alkylation process. Particularly, the invention provides a liquid alkylation catalyst composition which avoids many of the safety and environmental concerns associated with hydrofluoric acid by providing a liquid alkylation catalyst composition which overcomes many of the safety and environmental concerns associated with concentrated hydrofluoric acid.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used hydrofluoric or sulfuric acid catalysts under relatively low temperature conditions. Acid strength is preferably maintained at 88 to 94 weight percent by the continuous addition of fresh acid and the continuous withdrawal of spent acid.

Hydrofluoric acid and sulfuric acid alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381-397, (1988). For a survey of hydrofluoric acid catalyzed alkylation, see 1 *Handbook of Petroleum Refining Processes* 23-28 (R. A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry used anhydrous hydrogen fluoride primarily as a liquid catalyst for alkylation of olefinic hydrocarbons to produce alkylate for increasing the octane number of gasoline. Years of experience in its manufacture and use have shown that HF can be handled safely, provided the hazards are recognized and precautions taken. Though many safety precautions are taken to prevent leaks, massive or catastrophic leaks are feared primarily because the anhydrous acid will fume on escape creating a vapor cloud that can be spread for some distance. Previous workers in this field approached this problem from the standpoint of containing or neutralizing the HF cloud after its release.

U.S. Pat. Nos. 4,938,935 and 4,985,220 to Audeh and Greco, as well as U.S. Pat. No. 4,938,936 to Yan teach various methods for containing and/or neutralizing HF acid clouds following accidental releases.

But it would be particularly desirable to provide an additive which decreases the cloud forming tendency of HF without compromising its activity as an isoparaffin:olefin alkylation catalyst. Solvents and complexing agents for hydrofluoric acid complexes have, in the past, been disclosed for various purposes as noted in the following references.

U.S. Pat. No. 2,615,908 to McCaulay teaches thioether-HF-copper complex compounds and a method for preparing the same. Potential uses for the thioether-HF-copper complex compounds are listed from column 6, line 55 through column 8 at line 3. The method is said to be useful for purifying HF-containing vent gases from an industrial HF alkylation plant. See column 7, lines 10-24.

U.S. Pat. No. 3,531,546 to Hervert discloses a HF-$CO_2$ catalyst complex which is said to be useful for alkylation as well as olefin isomerization.

U.S. Pat. No. 3,795,712 to Torck et al. relates to acid catalysts comprising a Lewis acid, a Bronsted acid, and a sulfone of the formula $R-SO_2-R'$, where R and R' are each separately a monovalent radical containing from 1 to 8 carbon atoms or form together a divalent radical having from 3 to 12 carbon atoms.

U.S. Pat. No. 3,856,764 to Throckmorton et al. teaches an olefin polymerization catalyst comprising (1) at least one organoaluminum compound, (2) at least one nickel compound selected from the class consisting of nickel salts of carboxylic acids, organic complex compounds of nickel, or nickel tetracarbonyl and (3) at least one hydrogen fluoride complex prepared by complexing hydrogen fluoride with a member of the class consisting of ketones, ethers, esters, alcohols, nitriles, and water.

U.S. Pat. No. 4,636,488 discloses an anhydrous nonalcoholic alkylation catalyst comprising a mixture of a mineral acid and an ether in proportions of from about 50 to about 99 weight percent of mineral acid and from about 1 to about 50 weight percent of ether. Useful mineral acids include HF; see column 4 at lines 56-60.

Promoters such as alcohols, thiols, water, ethers, thioethers, sulfonic acids, and carboxylic acids are disclosed in combination with strong Bronsted acids such as HF, fluorosulfonic and trihalomethanesulfonic acids in U.S. Pat. No. 3,778,489 to Parker et al. The promoters are said to modify the activity of the strong Bronsted acids for alkylation.

The preceding references describe catalyst complexes containing strong Bronsted acids which are useful as catalysts for various reactions. In view of the increasing safety and environmental concerns surrounding the cloud-forming tendency of hydrofluoric acid, providing an alternative catalyst composition with catalytic properties essentially equivalent to hydrofluoric acid while avoiding the safety and environmental concerns associated with concentrated hydrofluoric acid would be a major advance in the art. Moreover, it would be particularly beneficial to provide a catalyst composition which can readily be substituted for concentrated hydrofluoric acid in a commercial riser-type hydrofluoric acid isoparaffin:olefin alkylation process unit.

SUMMARY OF THE INVENTION

In accordance with the present invention, it has been found that carbonates having the formula ROC(O)OR or

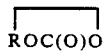
ROC(O)O are effective additives to suppress the vapor-forming tendency of strong acids such as HF but, surprisingly, have only minor effects on isoparaffin:olefin alkylation activity. The mechanism underlying this unusual phenomenon is not well understood; indeed, this development contradicts the reasonable expectation that dilution would degrade HF catalyst performance. The result is particularly surprising because years of industrial experience have proven that maintaining acid strength in commercial HF alkylation process units is critical to alkylate product quality, with loss of acid strength precipitating immediate degradation in alkylate product quality.

The invention provides, in a first aspect, an alkylation catalyst composition comprising from about 10 to about 90 weight percent of at least one acid selected from the group consisting of hydrofluoric acid and the halogen-substituted sulfonic acids, together with from about 10 to about 90 weight percent of an additive having the formula ROC(O)OR or

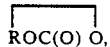
ROC(O) O, wherein R is selected from alkyl, alkyl halide, aromatic and halogenated aromatic groups having from about 1 to about 30 carbon atoms, preferably from about 1 to about 10 carbon atoms, more preferably from about 1 to about 6 carbon atoms. Of the useful halides (members of Group VIIA of the Periodic Table of the Elements, fluorine is particularly preferred. The terms "alkyl halide" and "halogenated aromatic" as used herein refer to R groups containing at least one halogen substituent. Examples of useful halogenated sulfonic acids include chlorosulfonic, fluorosulfonic, difluoromethanesulfonic, trifluoromethanesulfonic, and perfluoroalkanesulfonic acids.

The invention further provides, in a second aspect, a process for alkylating an isoparaffin with an olefin comprising effecting reaction of isoparaffin and olefin with an alkylation catalyst composition comprising from about 10 to about 90 weight percent of at least one selected from the group consisting of hydrofluoric acid and the halogen-substituted sulfonic acids together with from about 10 to about 90 weight percent of a carbonate additive having the formula ROC(O)OR or

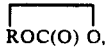
ROC(O) O, wherein R is selected from alkyl, alkyl halide, aromatic and halogenated aromatic groups having from about 1 to about 30 carbon atoms, preferably from about 1 to about 10 carbon atoms, more preferably from about 1 to about 6 carbon atoms.

DETAILED DESCRIPTION

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44-56, the disclosure of which is incorporated by reference as if set forth at length herein.

The molar ratio of isoparaffin to olefin is generally from about 1:1 to about 100:1, preferably from about 1:1 to about 50:1, and more preferably from about 5:1 to about 20:1.

Carbonate Additives

The catalyst composition of the present invention comprises from about 10 to about 90 weight percent of at least one selected from the group consisting of hydrofluoric acid and the halogen-substituted sulfonic acids together with from about 10 to about 90 weight percent of a carbonate having the formula ROC(O)OR or

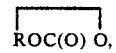
ROC(O) O, wherein R is an alkyl or an alkyl halide, or an aromatic or halogenated aromatic group having from about 1 to about 30 carbon atoms, preferably from about 1 to about 10 carbon atoms, more preferably from about 1 to about 6 carbon atoms. Propylene carbonate

($C_3H_6OC(O)O$ is a particularly preferred carbonate additive, and tetrachloroethylene carbonate is an example of a suitable alkyl halide-containing additive. The alkylation catalyst complex of the invention preferably comprises from about 10 to about 90 weight percent of the carbonate additive, more preferably from about 20 to about 80 weight percent of the carbonate additive, with the substantial balance of the HF/carbonate catalyst complex comprising HF. The catalyst complex of the invention is preferably free of intentionally added water, and still more preferably, is anhydrous. While all halides are suitable when R is an alkyl halide or halogenated aromatic, fluorine is preferred.

Process Conditions

The catalyst composition of the invention may be readily substituted for concentrated hydrofluoric acid in a conventional hydrofluoric acid alkylation process unit, for example, a riser-type hydrofluoric acid alkylation process unit. Equipment modifications required to complete the catalyst changeover typically include the installation of additive separation and recovery facilities.

The present alkylation process is suitably conducted at temperatures of from about 10° to about 100° C., preferably from about 20° to about 80° C., and more preferably from about 25° C. to about 50° C. Lower reaction temperatures within the disclosed ranges are preferred to maximize alkylate octane and yield. The upper temperature limit is critical to avoid undesirable side reactions, such as isomerization, cracking and oligomerization. Operating temperature typically falls within the range of about 25° to about 40° C. The alkylation process may be operated at pressures ranging from 1 to 1000 psig, and more preferably from about 10 to about 500 psig. The olefin feed rate may suitably range from 0.01 to 10 $hr^{-1}$ weight hourly space velocity (WHSV), and preferably falls within the range of 0.05 to 5 $hr^{-1}$ WHSV. The mixed isoparaffin:olefin feed may be contacted with the alkylation catalyst composition in a suitable vessel such as a stirred tank or riser-type reactor. Contact times for isoparaffin:olefin feed with the catalyst composition of the invention typically fall within the range of about 10 seconds to about 20 minutes.

The carbonate additive component of the alkylation catalyst composition may be injected directly into the alkylation process reaction zone, or may be mixed with the hydrocarbon charge, or may be admixed with fresh hydrofluoric acid prior to charging the fresh acid to the alkylation process reaction zone. Downstream from the alkylation reaction zone, the catalyst composition is preferably separated from the reactor effluent stream and recycled to the alkylation reaction zone. Purification of the catalyst composition may be required to maintain acid strength and alkylation activity. In this case, separation of HF and carbonate additive from less desirable side-products may be required. The particular separation technique selected, however, depends upon several factors, non-limiting examples of which include the characteristics of the R substituent group, (e.g., the length of the alkyl chain of the carbonate), the catalyst/alkylate separator conditions, and the composition of the feedstock.

Embodiment

In a typical commercial embodiment, the effluent stream from the alkylation reaction zone is separated, e.g., decanted, into an alkylate-rich hydrocarbon stream and an acid recycle stream. The alkylate-rich hydrocarbon stream is typically fractionated further to provide an isoparaffin recycle stream to the alkylation reaction zone. In the present invention, the preferred method for recycling the carbonate additive to the alkylation reaction zone may vary with the particular carbonate employed. Decanting the alkylation reaction zone effluent to separate alkylate-rich hydrocarbon from the HF/propylene carbonate mixture has been found to yield relatively pure hydrocarbon and HF/propylene carbonate streams. Separation and recycle of the propylene carbonate is preferably integrated with the acid purification steps of a typical commercial HF alkylation process unit.

The alkylation reaction zone effluent is first separated (e.g., decanted) into an alkylate-rich hydrocarbon stream and a liquid catalyst dream containing HF and propylene carbonate. A portion of the catalyst stream is then derived to an acid purification stage where high-boiling hydrocarbons (commonly referred to as acid soluble oil (ASO) and comprising conjunct polymer byproducts of the isoparaffin:olefin alkylation reaction) are separated (e.g., distilled) from the lower-boiling HF acid. Because propylene carbonate has a normal boiling point of about 240° C., it typically remains with the ASO effluent from the acid purification stage, and must be separated from the ASO so that the propylene carbonate can be recycled. The feedstock composition, as well as the process conditions, among other factors, effect the ASO boiling range, and, therefore, influence the selection of a most preferred ASO/propylene carbonate separation method. If the boiling range overlap between the ASO and the propylene carbonate is minimal, distillation can be a suitable technique. However, if the ASO boiling range overlaps that of the (propylene) carbonate additive, separation techniques such as liquid/liquid extraction or selective sorption may be employed. The ASO is then disposed of in accordance with proper environmental and safety procedures and the propylene carbonate is recycled to the alkylation reaction zone.

EXAMPLES

The following Examples 1-3 demonstrate the effectiveness of the HF/carbonate catalyst composition of the invention for catalyzing isoparaffin:olefin alkylation. Example 1 demonstrates the well-known effectiveness of anhydrous HF as an isoparaffin:olefin alkylation catalyst and is presented for comparison to evaluate the effectiveness of various carbonate additives (Examples 2 and 3).

EXAMPLE 1—COMPARATIVE

Anhydrous HF (40 grams, obtained from Matheson Chemical Company of Bridgeport, New Jersey) was condensed into a clean, dry autoclave (1000 cc). Isobutane (100 grams) was added, and the autoclave was stirred at 1500 rpm. The autoclave was pressurized to 100 psig and brought to room temperature (22° C., 71° F.). A pre-mixed 10:1 weight:weight mixture of isobutane:2-butene feed (obtained from Matheson Chemical Company) was added at a rate of 250 cc/hour for 2 hours under autogeneous pressure for a total isobutane:2-butene charge of 500 cc. An 8°-12° F. (4°-7° C.) temperature rise was observed during feed addition resulting in an average reaction temperature of 26°-28° C. (79°-83° F.). The autoclave was sampled (300 cc) immediately after feed addition was complete. The sample was flashed at room temperature and quenched with a chilled water trap. Samples of the liquid and gas products were analyzed by capillary GC (60m DB-1 column). The results of Example 1 are shown in the table below.

EXAMPLES 2 AND 3

HF/propylene carbonate catalysts were evaluated for isoparaffin/olefin alkylation with a 10/1 wt/wt isobutane/2-butene feed at 80.F in a semi-batch autoclave. In Examples 2 and 3, 10 and 26.7 grams of propylene carbonate, respectively, (Aldrich Chemical Co.) were added to a clean, dry autoclave (1000 cc). The autoclave was sealed, cooled with liquid nitrogen and placed under vacuum. Anhydrous HF (40 grams, Matheson) was then condensed into the autoclave. Isobutane (100 grams) was added, and the autoclave was stirred at 1500 rpm. The autoclave was pressurized to 100 psig and brought to room temperature 22° C. (71° F.). A pre-mixed 10/1 wt/wt isobutane/2-butene feed (Matheson) was then added (500 cc at a rate of 250 cc/hr) under autogenous pressure. An 8°-12° F. (4°-7° C.) temperature rise was observed during feed addition resulting in an average reaction temperature of 26°-28° C. (79°-83° F.) The autoclave was sampled (300 cc) immediately after feed addition was complete. The sample was flashed at room temperature and quenched with a chilled water trap. Samples of the liquid and gas products were analyzed by capillary GC (60m DB-1 column).

Results from experiments conducted with pure HF and HF/propylene carbonate mixtures are given in the table below. The HF/carbonate mixtures tested (80/20 and 60/40 wt/wt) were liquids which fumed mildly in air. The physical appearance of the HF/carbonate mixtures indicated that the vapor pressure of HF had been significantly reduced. However, alkylation performance was only slightly diminished upon adding up to 40 wt % propylene carbonate to HF. The ratio of high octane trimethylpentanes to lower octane dimethylhexanes in the alkylate product decreased slightly from 9.2 with a pure HF catalyst to 8.2 with a 80/20 wt/wt HF/propylene carbonate catalyst. Also, the amount of heavy C$_9$+alkylate increased from 6.4 wt % to only 7.0 wt % with the 80/20 catalyst. The results demonstrate the efficacy of carbonate compounds as additives for HF.

TABLE

| Semi-Batch Evaluation of HF/Propylene Carbonate | | | |
|---|---|---|---|
| | Example 1 | Example 2 | Example 3 |
| Catalyst | HF | HF/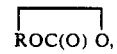C$_3$H$_6$OC(O)O | HF/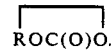C$_3$H$_6$OC(O)O |
| Appearance | Fuming | (80/20 wt/wt) Liquid | (60/40 wt/wt) Liquid |
| HF/additive (mol/mol) | 0 | 20/1 | 8/1 |
| Alkylate product, wt. % | | | |
| C$_5$-C$_7$ | 5.5 | 6.6 | 9.9 |
| C$_8$ | 88.1 | 86.4 | 75.0 |
| C$_9$+ | 6.4 | 7.0 | 15.1 |
| TMP/DMH | 9.2 | 8.2 | 6.0 |
| Olefin Conv. % | 99.9 | 98.8 | 97.0 |

Changes and modifications in the specifically described embodiments can be carried out without departing from the scope of the invention which is intended to be limited only by the scope of the appended claims.

What is claimed is:

1. A process for alkylating an isoparaffin with an olefin comprising effecting reaction of isoparaffin and olefin with an alkylation catalyst composition comprising from about 10 to about 90 weight percent of at least one said selected from the group consisting of hydrofluoric acid and the halogen-substituted sulfonic acids, together with from about 10 to about 90 weight percent of an additive having the formula ROC(O)OR or

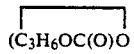
ROC(O)O, wherein R is selected form alkyl, alkyl halide, aromatic and halogenated aromatic groups having from about 1 to about 30 carbon atoms.

2. The process of claim 1 wherein R contains from about 1 to about 10 carbon atoms.

3. The process of claim 2 wherein R contains from about to about 6 carbon atoms.

4. The process of claim 1 wherein R is an alkyl group.

5. The process of claim 1 wherein R is an alkyl halide group.

6. The process of claim 1 wherein R is an aromatic group.

7. The process of claim 1 wherein R is a halogenated aromatic group.

8. The process of claim 3 wherein said additive is propylene carbonate.

9. The process of claim 1 wherein said alkylation catalyst composition comprises from about 10 to about 80 weight percent of an additive having the formula ROC(O)OR or

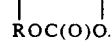
ROC(O)O.

10. The process of claim 1 wherein said alkylation catalyst composition comprises from about 20 to about 60 weight percent of an additive having the formula ROC(O)OR or

ROC(O)O.

11. The process of claim 1 further comprising charging said isoparaffin and said olefin to a riser reactor containing said alkylation catalyst composition.

12. The process of claim 11 further comprising controlling residence time of said isoparaffin and said olefin within said riser reactor to convert at least a portion of said olefin and said isoparaffin to alkylate gasoline.

13. A process for alkylating an isoparaffin with an olefin comprising effecting reaction of isoparaffin and olefin with an alkylation catalyst composition comprising from abut 10 to about 90 weight percent hydrofluoric acid and from about 10 to about 90 weight percent of an additive having the formula ROC(O)OR or

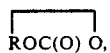
ROC(O) O, wherein R is selected from alkyl, alkyl halide, aromatic and halogenated aromatic groups having from about 1 to about 30 carbon atoms, wherein said alkylation catalyst composition is a substantially nonfuming liquid at atmospheric temperature and pressure and wherein said process produces an alkylate product from a given feedstock having a ration of trimethylpentanes to dimethylhexanes of at least 65 percent of the ratio of trimethylpentanes to dimethylhexanes of the alkylate product produced by contacting said given feedstock with neat HF under like conversion conditions.

14. The process of claim 13 wherein R contains from about 1 to about 10 carbon atoms.

15. The process of claim 14 wherein R contains from about 1 to about 6 carbon atoms.

16. The process of claim 13 wherein R is an alkyl group.

17. The process of claim 13 wherein R is an alkyl halide group.

18. The process of claim 13 wherein R is an aromatic group.

19. The process of claim 13 wherein R is a halogenated aromatic group.

20. The process of claim 16 wherein said additive is propylene carbonate.

21. The process of claim 13 wherein said alkylation catalyst composition comprises from about 10 to about 80 weight percent of an additive having the formula ROC(O)OR or

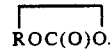
ROC(O)O.

22. The process of claim 21 wherein said alkylation catalyst composition comprises from about 20 to about 60 weight percent of an additive having the formula ROC(O)OR or

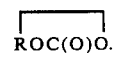
ROC(O)O.

23. The process of claim 13 further comprising charging said isoparaffin and said olefin to a riser reactor containing said alkylation catalyst composition.

24. The process of claim 23 further comprising controlling residence time of said isoparaffin and said olefin within said riser reactor to convert at least a portion of said olefin and said isoparaffin to alkylate gasoline.

* * * * *

UNITED STATES PATENT AND TRADEMARK OFFICE
CERTIFICATE OF CORRECTION

PATENT NO. : 5,220,096

DATED : June 15, 1993

INVENTOR(S) : Kenneth J. Del Rossi

It is certified that error appears in the above-identified patent and that said Letters Patent is hereby corrected as shown below:

Col. 8, line 10, "form" should be --from--

Col. 8, line 16, after "about" add --1--

Signed and Sealed this

Thirty-first Day of May, 1994

Attest:

BRUCE LEHMAN

Attesting Officer

Commissioner of Patents and Trademarks